United States Patent
Anglada

(10) Patent No.: US 8,603,018 B2
(45) Date of Patent: Dec. 10, 2013

(54) WRIST ORTHOSIS FOR TREATING CARPAL TUNNEL SYNDROME

(75) Inventor: Gerard Anglada, Saint Etienne (FR)

(73) Assignee: Gibaud, Saint Etienne (FR)

( * ) Notice: Subject to any disclaimer, the term of this patent is extended or adjusted under 35 U.S.C. 154(b) by 440 days.

(21) Appl. No.: 12/933,530

(22) PCT Filed: Feb. 2, 2009

(86) PCT No.: PCT/FR2009/000114
§ 371 (c)(1),
(2), (4) Date: Dec. 6, 2010

(87) PCT Pub. No.: WO2009/115661
PCT Pub. Date: Sep. 24, 2009

(65) Prior Publication Data
US 2011/0077569 A1    Mar. 31, 2011

(30) Foreign Application Priority Data

Mar. 21, 2008   (FR) ......................... 08 1568

(51) Int. Cl.
*A61F 5/00*    (2006.01)
*A63B 57/00*   (2006.01)

(52) U.S. Cl.
USPC ........................................ 602/21; 473/213

(58) Field of Classification Search
USPC .............. 602/21, 20, 5, 1; 473/131, 207, 212, 473/213
See application file for complete search history.

(56) References Cited

U.S. PATENT DOCUMENTS

| | | | | |
|---|---|---|---|---|
| 3,707,963 A | * | 1/1973 | Keropian | 602/21 |
| 5,358,471 A | * | 10/1994 | Klotz | 602/21 |
| 5,484,394 A | * | 1/1996 | Singer et al. | 602/16 |
| 6,293,918 B1 | | 9/2001 | Wang | |
| 6,827,653 B2 | * | 12/2004 | Be | 473/62 |
| 7,156,819 B2 | * | 1/2007 | Sieller et al. | 602/21 |
| 2007/0276305 A1 | | 11/2007 | Kahlmeyer et al. | |

FOREIGN PATENT DOCUMENTS

GB    2 184 659 A    7/1987
WO    95/25489 A1    9/1995

OTHER PUBLICATIONS

International Search Report issued in PCT/FR2009/000114, Aug. 6, 2009.

* cited by examiner

*Primary Examiner* — Patricia Bianco
*Assistant Examiner* — Tarla Patel
(74) *Attorney, Agent, or Firm* — Workman Nydegger

(57) ABSTRACT

An orthosis including a proximal portion consisting of an armband and a strap around the forearm as well as a distal portion consisting of a palm support and a strap around the hand. The support is pivotable relative to the armband about a transverse pivot axis which substantially coincides with the flexion/extension axis of the user's wrist joint when the orthosis is being worn by a user. The orthosis further comprises pivotal locking means for use in a desired angular position.

13 Claims, 4 Drawing Sheets

WRIST ORTHOSIS FOR TREATING CARPAL TUNNEL SYNDROME

FIELD OF THE INVENTION

The present invention concerns a wrist orthosis for treating carpal tunnel syndrome (inflammation of the flexor muscles).

BACKGROUND

Pathologies of the carpal tunnel region can require surgery. However, it is known that this operation can be avoided in 50% of cases if, upon the appearance of the first symptoms, the flexing of the wrist is stopped, in particular at night.

Thus, already known are orthoses designed to prevent flexing of the user's wrist. Initially, when the symptoms are the most significant, it is recommended to place the wrist in a treatment position corresponding to a certain degree of extension and prevent the flexing of the wrist from that position. Subsequently, depending on the user's recovery, and gradually, the treatment position can correspond to a lesser degree of extension, or even a certain degree of flexing, flexing past that position still being blocked.

Orthoses of this type custom made by an orthotist are already known. They consist of a rigid piece held around the wrist and forearm by straps, this rigid piece defining a determined treatment position. Depending on the evolution of the user's symptoms, the orthotist modifies the treatment position. To that end, this type of orthosis is made in a material that, when it exceeds a certain temperature, becomes malleable, and becomes rigid again after cooling. For example, the orthosis is made of resin and the orthotist submerges it in hot water to be able to then remodel it and adapt it to the stage of the user's healing by setting the appropriate degree of extension or flexing.

These orthoses therefore require intervention by a qualified orthotist, and cannot be adapted by the users themselves. Moreover, the operations for changing the treatment position, i.e. the angle of extension or flexing, are relatively long. To avoid interrupting treatment for several days, this therefore involves bringing the orthosis to the specialist when the latter is available to perform the remodeling, and to come pick it up quickly after this remodeling is done. Of course, this moment must also correspond to the moment when the evolution of the symptoms requires a modification of the treatment position defined by the orthosis. All of this is particularly restrictive.

Also known are orthoses comprising a proximal portion designed to grip the forearm and a distal portion designed to grip the hand, in which the angle between the proximal and distal portions can be modified, by relative pivoting around an axis essentially combined with the flexion/extension axis of the user's wrist joint.

However, these known orthoses are not fully satisfactory, in particular for issues regarding ease of implementation and quality of the maintenance.

SUMMARY

The present invention aims to resolve the aforementioned drawbacks.

To that end, the invention concerns a wrist orthosis comprising:
- a proximal portion designed to grip the forearm;
- a distal portion designed to grip the hand;
- pivot means for the proximal and distal portions in relation to each other, around a transverse pivot axis that, when the orthosis is worn by a user, is essentially combined with the flexion/extension axis of the user's wrist joint;
- means for locking the pivot means in a desired angular position.

Furthermore, according to the invention, this orthosis is such that:
- the proximal portion includes an essentially rigid armband designed to be placed against the rear face of the forearm and a flexible strap attached to the armband and designed to pass against the front face of the forearm, such that the forearm is gripped between the armband and the strap;
- and the distal portion includes an essentially rigid support designed to be placed under the palm of the hand and a flexible strap connected to the support and designed to pass against the back of the hand, such that the hand is gripped between the support and the strap.

Owing to the invention, it becomes very easy and quick to modify the treatment position by a simple actuation of the pivot means, then locking of the distal portion in relation to the proximal portion in the desired angular position. The appropriate treatment position can be defined by a doctor, depending on the evolution of the pains felt by the user, whereas the operation modifying the relative angle can be done by the user himself.

Consequently, the evolution of the shape of the orthosis can very precisely follow the user's progressive recovery. The invention therefore provides an orthosis that is particularly well adapted to all of the stages of healing of the user's pathology and, in fine, allowing improved carpal tunnel syndrome treatment.

Furthermore, the fact that the rigid portions of the orthosis are placed "on" the arm and "under" the hand, respectively, is very advantageous since, owing to that arrangement, a lever arm effect is obtained that guarantees excellent maintenance of the orthosis.

This maintenance is obtained with less significant pressure than if the two rigid portions were situated on the same side, i.e. only on the front—or rear—of the forearm and the hand. Indeed, with the arrangement according to the invention, it is not necessary to tighten the straps as much as in the prior art to ensure that maintenance. This results in decreased compression, therefore increased comfort and reduced vascular risks for the user.

Moreover, the orthosis according to the invention is particularly adapted to treatment of carpal tunnel syndrome due to the absence of any rigid portion under the carpal tunnel. Wearing comfort is also increased.

The expression "essentially rigid" is used for the armband as opposed to the strap, which is completely flexible and deformable. But this does not rule out that the armband can have a certain capacity to be elastically deformed according to a small amplitude. The presence of an essentially rigid armband makes the orthosis easier for the user to put on and adjust than if the orthosis were fixed around the forearm only by a set of straps.

The orthosis can also include means for limiting the pivot amplitude of the distal portion in relation to the proximal portion in an angular range extending on either side of the neutral position. The neutral position corresponds to a position in which the orthosis wearer's wrist is not flexed or extended. This limiting means constitutes a safety device, because it makes it possible to prevent the orthosis from forming too significant an angle, which could be detrimental to the user's healing.

According to one possible embodiment, the orthosis comprises means for adjusting the angle between the distal portion and the proximal portion according to discrete angle values, for example 5° in 5°.

DESCRIPTION OF THE DRAWINGS

We will now describe a non-limiting example of one possible embodiment of the invention, in reference to the appended figures.

DETAILED DESCRIPTION OF VARIOUS EMBODIMENTS

Figure 1:
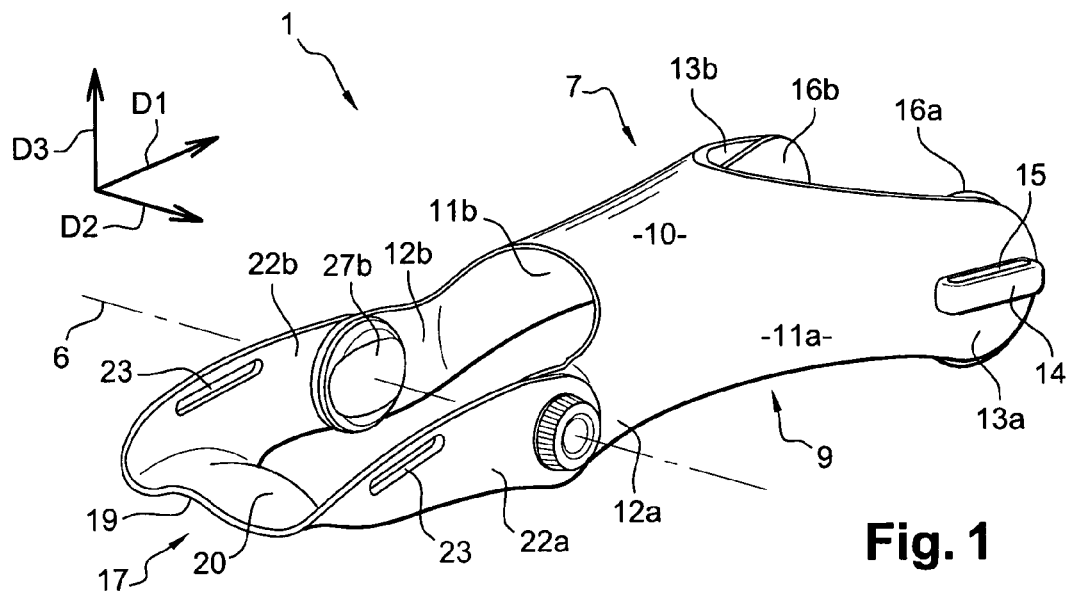
FIG. 1 is a front perspective view of an orthosis according to the invention.

As illustrated in the figures, an orthosis 1 according to the invention comprises a proximal portion 2 designed to grip a user's forearm 3 and a distal portion 4 designed to grip the user's hand 5.

The longitudinal direction D1 is defined as the general direction in which the forearm extends (when the orthosis 1 is worn), the transverse direction D2 as the direction of the flexion/extension axis of the user's wrist joint and the vertical direction D3 as the adduction/abduction wrist joint direction.

The terms "proximal" and "distal" are used in reference to direction D1 and the term "lateral" in reference to direction D2.

The proximal 2 and distal 4 portions form two distinct pieces that can pivot in relation to each other around a transverse pivot axis 6 that, when the orthosis 1 is worn by a user, is essentially combined with the flexion/extension axis of the user's wrist joint.

We will first describe the proximal portion 2.

The proximal portion 2 includes an essentially rigid armband 7, for example made of a plastic material or resin, and a flexible strap 8 connected to the armband 7 (see FIGS. 6 and 7a to 7e).

In the illustrated embodiment, the armband 7 includes:

a main portion 9 in cradle form that, when the orthosis 1 is worn by a user, covers the forearm, said main portion 9 comprising a central portion 10 placed against the rear face of the forearm and two lateral portions 11a, 11b arranged on either side of the forearm;

two distal lateral pads 12a, 12b extending essentially longitudinally in the distal direction each from a lateral portion 11a, 11b of the main portion 9, on either side of the forearm, the pivot axis 6 being situated essentially at the distal portion of said distal lateral pads 12a, 12b.

The armband 7 also includes two lateral proximal pads 13a, 13b extending essentially longitudinally in the proximal direction each from a lateral portion 11a, 11b of the main portion 9, on either side of the forearm, said proximal lateral pads 13a, 13b forming a fork that can be slightly elastically deformed. Thus, by choosing an adapted spacing between the proximal lateral pads 13a, 13b, one can obtain slight gripping of the forearm by spring effect of that fork and, as a result, better holding of the armband 7 transversely around the forearm. One also ensures homogenous pressure on the forearm.

The two proximal lateral pads 13a, 13b of the armband 7 comprise fastening means 14 of the strap 8 here formed by members protruding toward the outside and provided with a longitudinal slot 15 for the passage of the strap 8.

The orthosis can also include bearing members 16a, 16b situated at the proximal end portion of the proximal lateral pads 13a, 13b, these bearing members 16a, 16b facing the inside of the orthosis 1 opposite each other. These bearing members make it possible to ensure better maintenance of the orthosis on the user's forearm, without excessive gripping, which is even more important when the orthosis is intended to be worn at night. To that end, they can be made of an anti-slip material, such as silicone.

Figure 2:
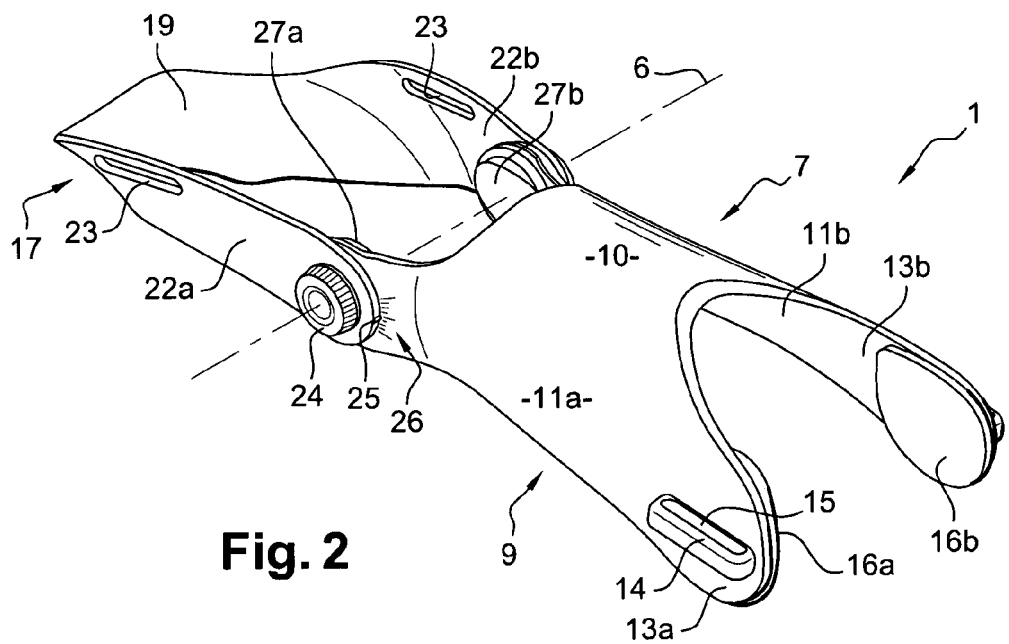
FIG. 2 is a rear perspective view of the orthosis.
Figure 3:
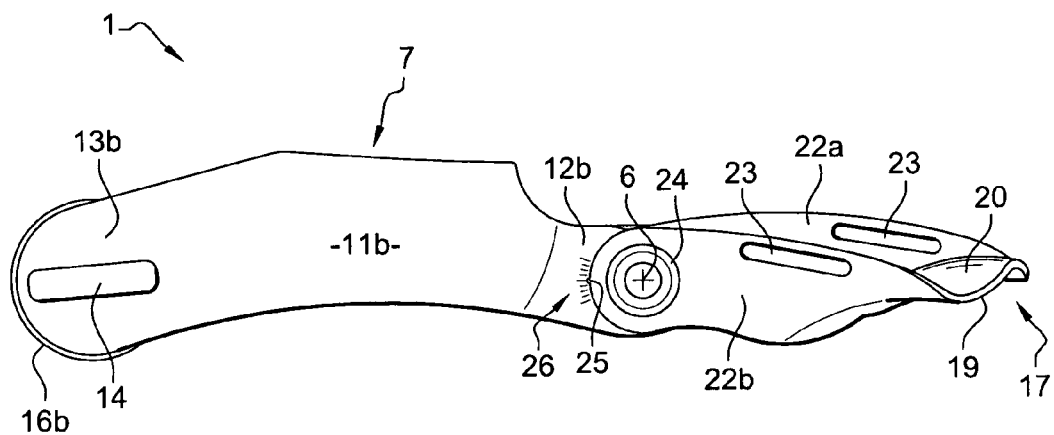
FIG. 3 is a side view of the orthosis.
Figure 4:
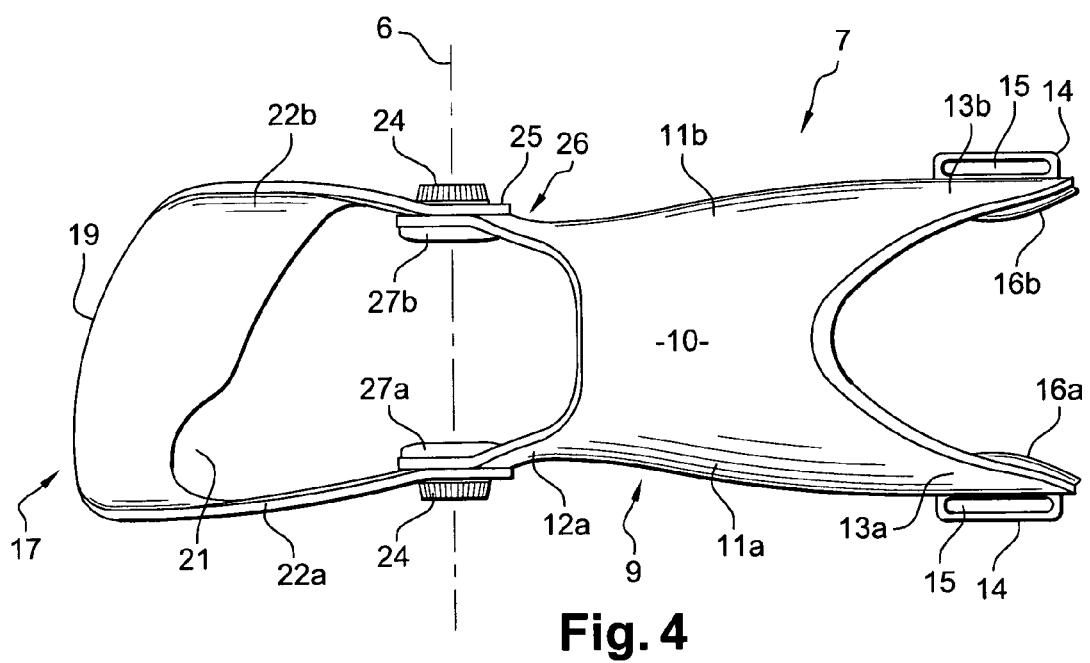
FIG. 4 is a top view of the orthosis.
Figure 5:
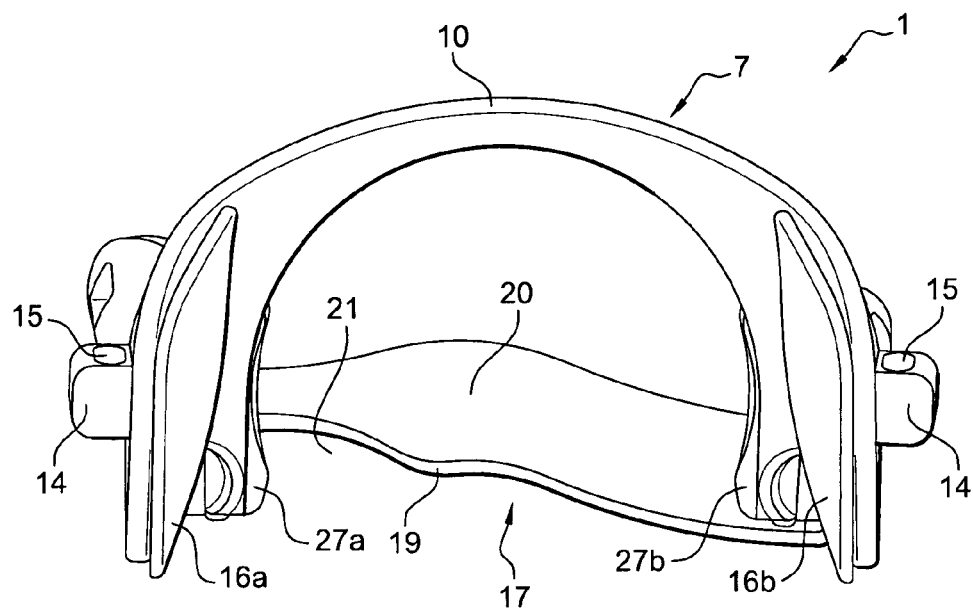
FIG. 5 is a rear view of the orthosis.
Figure 6:
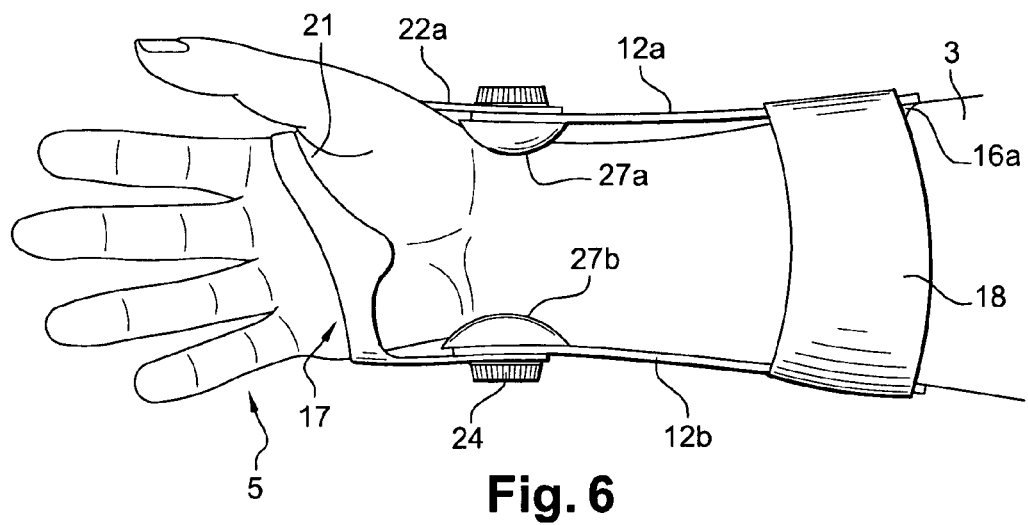
FIG. 6 is a bottom view of the orthosis worn by a user.

Advantageously, the bearing members 16a, 16b can have a channel shape curved in an essentially longitudinal direction, as shown more particularly in FIG. 2. This channel shape fits the shape of the forearm and further improves the maintenance.

We will now describe the distal portion 4.

The distal portion 4 includes an essentially rigid support 17, for example made of a plastic material or resin, designed to be placed under the palm of the hand, and a flexible strap 18 connected to the support 17 and designed to pass against the back of the hand (see FIGS. 6 and 7a to 7e).

In the illustrated embodiment, the support 17 includes:

a central portion 19 including, on one hand, a boss 20 whereof the shape is arranged to fit the shape of the palm, and on the other hand, a recess 21 designed to receive the thumb—index commissure and allow the passage of the thumb under the support 17;

two lateral walls 22a, 22b extending from the essentially longitudinal portion 19 in the proximal direction, on either side of the hand, the pivot axis 6 being situated essentially at the proximal end portion of said lateral walls 22a, 22b.

The two lateral walls 22a, 22b of the support 17 comprise means 23 for attaching the strap 18 here made up of passage orifices for the strap 18, oriented essentially longitudinally.

The armband 7 and the support 17 are connected to each other via pivot means around the predefined axis 6. In the assembled position, the proximal end portion of each lateral wall 22a, 22b of the support 17 is in contact, transversely, with a distal end portion of the corresponding distal lateral pad 12a, 12b of the armband 7. In the vicinity of the pivot axis 6, the lateral walls 22a, 22b are thus superimposed on the distal lateral pads 12a, 12b, while being situated outside thereof.

The orthosis 1 also comprises means for limiting the pivot amplitude of the support 17 in relation to the armband 7, in an angular range extending on either side of the neutral position. For example, the relative pivoting happens in a range of ±20° around said neutral position. A positive angle Θ between the support 17 and the armband 7 corresponds to an extended position of the hand, while a negative angle Θ corresponds to a flexed position of the hand.

Advantageously, the orthosis also comprises means for adjusting the angle Θ between the support 17 and the armband 7 according to discrete angle values, for example 5° in 5°, as well as means for locking the pivot means in a desired angular position.

According to one possible embodiment, the connection between the armband 7 and the support 17 is obtained using a toothing with small dimensions (not visible in the figures) and a nut 24 accessible from the outside and forming an adjustment and tightening means for the user. In order to simplify the adjustment of the angle Θ, the or each lateral wall 22a, 22b of the support 17 can be provided with a proximal lug 25 arranged opposite an angular graduation 26 done on the corresponding distal lateral pad 12a, 12b of the armband 7.

Preferably, the orthosis 1 comprises bearing members 27a, 27b situated at the pivot axis 6 and facing the inside of the orthosis 1 opposite each other. These bearing members make it possible to ensure better maintenance of the orthosis on the user's forearm, without excessive gripping, which is particularly important in this case, where the orthosis is designed to be worn at night. To that end, the bearing members can be made of an anti-slip material, such as silicone. Furthermore, they make it possible to protect the user's wrist from the pivot means.

Advantageously, the bearing means 27a, 27b can have a channel shape curved in a longitudinal direction, as shown more particularly in FIG. 1. This channel shape fits the shape of the wrist and further improves maintenance.

FIGS. 6 and 7a to 7e show the orthosis 1 worn by a user.

The forearm 3 is gripped between the armband 7, the central portion 10 of which is placed against the rear face of the forearm, and the strap 8, passing against the front face of the forearm. The hand 5 is squeezed between the support 17, placed against the palm, and the strap 18, passing against the back of the hand, the thumb passing under the support 17. Owing to this arrangement, we obtain a lever arm effect that guarantees excellent maintenance of the orthosis 1.

FIGS. 7a to 7e show different relative angular positions between the support 17 and the armband 7.

Figure 7A:
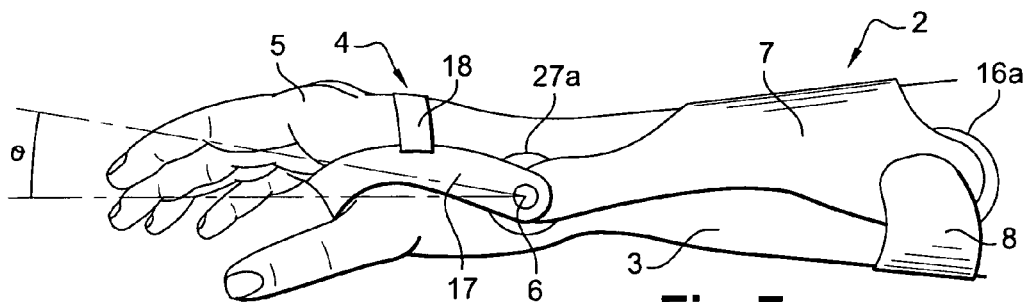
FIGS. 7a to 7e are side views of the orthosis worn by a user, with different angles between the distal portion and the proximal portion of the orthosis.
Figure 7B:
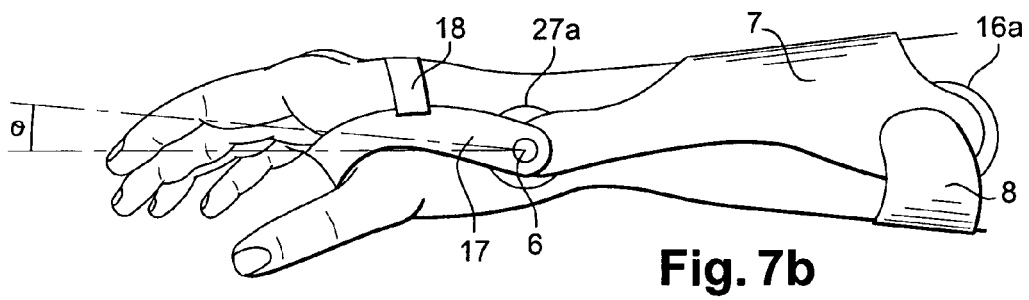
Figure 7C:
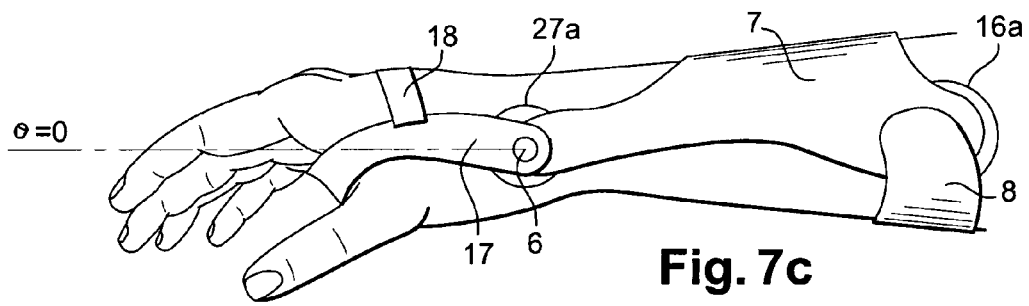
Figure 7D:
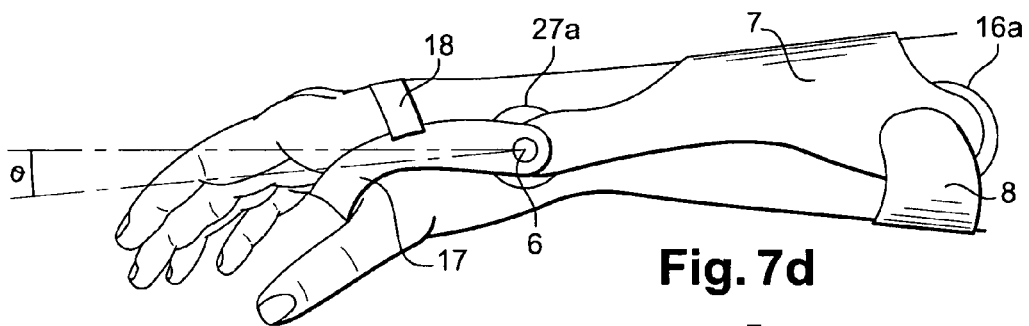
Figure 7E:
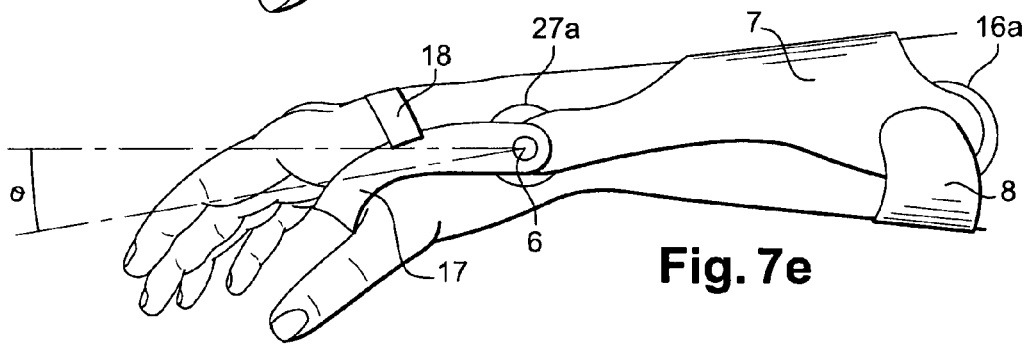

In FIG. 7c, the orthosis is in the neutral position, the angle Θ between the support 17 and the armband 7 being null. In this position, the orthosis user's wrist is neither flexed nor extended. In FIGS. 7a and 7b, the hand is extended, while in FIGS. 7d and 7e, the hand is flexed.

The orthosis 1 is intended to be worn at night by a user, who then cannot flex the hand beyond the angle Θ. The angle Θ is adjusted by the user according to his physician's instructions. For example, one can initially set a null angle Θ, and switch to an angle Θ of several degrees in extension if the pain intensifies. Conversely, one can go to an angle Θ of several degrees of flexion if the pain lessens and gradually increase the authorized flexion amplitude.

The orthosis 1 is especially simple for users to adjust by themselves. It does not require the intervention of a qualified orthotist to be customized. One need only provide a limited range of orthoses for the left and right wrist, in a certain number of sizes.

It goes without saying that the invention is not limited to the embodiment described above as an example, but that on the contrary it encompasses all alternative embodiments.

The invention claimed is:

1. A wrist orthosis, intended to treat carpal tunnel syndrome, comprising:
    a proximal portion designed to grip a forearm;
    a distal portion designed to grip a hand;
    pivot means of the proximal and distal portions in relation to each other, around a transverse pivot axis that, when the wrist orthosis is worn by a user, is essentially combined with the flexion/extension axis of the user's wrist joint;
    a connection for locking the pivot means in a desired angular position (Θ);
    wherein the proximal portion includes an essentially rigid armband designed to extend only against a rear face of the forearm and a flexible strap connected to the armband and designed to pass against a front face of the forearm, such that the forearm is gripped between the armband and the strap;
    and the distal portion includes an essentially rigid support designed to extend only under a palm of the hand and a flexible strap connected to the support and designed to pass against the back of the hand, such that the hand is gripped between the support and the strap.

2. The wrist orthosis according to claim 1, further comprising a safety device for limiting the pivot amplitude of the distal portion in relation to the proximal portion in an angular range extending on either side of the neutral position.

3. The wrist orthosis according to claim 1 wherein the connection is arranged for adjusting the angle (Θ) between the distal portion and the proximal portion according to discrete angle values.

4. The wrist orthosis according to claim 1, wherein the armband includes:
    a main portion in cradle form, which, when the orthosis is worn by a user, covers the forearm, said main portion comprising a central portion placed against the rear face of the forearm and two lateral portions arranged on either side of the forearm;
    two distal lateral portions extending essentially longitudinally in the distal direction, each from a lateral portion of the main portion, on either side of the forearm, the pivot axis being situated essentially at the distal end portion of distal lateral pads.

5. The wrist orthosis according to claim 4, wherein the armband also includes two proximal lateral pads extending essentially longitudinally in the proximal direction, each from a lateral portion of the main portion, on either side of the forearm, said proximal lateral pads forming a fork that can be slightly elastically deformable.

6. The wrist orthosis according to claim 5, further comprising bearing members situated at the proximal end portion of the proximal lateral pads, facing the inside of the orthosis opposite each other.

7. The wrist orthosis according to claim 6, wherein the bearing members have a channel shape curved in an essentially longitudinal direction.

8. The wrist orthosis according to claim 1, further comprising bearing members situated at the pivot axis and facing the inside of the orthosis opposite each other.

9. The wrist orthosis according to claim 1, wherein the support includes:
    a central portion including a boss whereof a shape is arranged to fit the shape of a palm, and a recess designed to receive a thumb-index commissure and allow the passage of a thumb under the support;
    two lateral walls extending from the essentially longitudinal central portion in the proximal direction, on either side of the hand, the pivot axis being situated essentially at the proximal end portion of said lateral walls.

10. The wrist orthosis according to claim 1, wherein the connection includes a nut for adjusting and tightening the proximal portion relative to the distal portion at the pivot axis.

11. The wrist orthosis according to claim 1, further comprising lateral walls of the proximal portion having a lug proximate the connection for measuring the desired angular position (Θ).

12. A wrist orthosis, intended to treat carpal tunnel syndrome, comprising:
    a proximal portion designed to grip a forearm;
    a distal portion designed to grip a hand;
    pivot means of the proximal and distal portions in relation to each other, around a transverse pivot axis that, when the wrist orthosis is worn by a user, is essentially combined with the flexion/extension axis of the user's wrist joint;

a nut for adjusting and tightening the proximal portion relative to the distal portion, and lateral walls of the proximal portion having a lug for measuring a desired angular position ($\Theta$);

wherein the proximal portion includes an essentially rigid armband designed to be placed against a rear face of the forearm and a flexible strap connected to the armband and designed to pass against a front face of the forearm, such that the forearm is gripped between the armband and the strap;

and the distal portion includes an essentially rigid support designed to be placed under a palm of the hand and a flexible strap connected to the support and designed to pass against the back of the hand, such that the hand is gripped between the support and the strap.

13. A wrist orthosis, intended to treat carpal tunnel syndrome, comprising:

a proximal portion designed to grip a forearm;

a distal portion designed to grip a hand;

pivot means of the proximal and distal portions in relation to each other, around a transverse pivot axis that, when the wrist orthosis is worn by a user, is essentially combined with the flexion/extension axis of the user's wrist joint;

wherein the proximal portion includes an essentially rigid armband designed to be placed against the rear face of the forearm and a flexible strap connected to the armband and designed to pass against the front face of the forearm, such that the forearm is gripped between the armband and the strap;

and the distal portion includes an essentially rigid support designed to be placed under the palm of the hand and a flexible strap connected to the support and designed to pass against the back of the hand, such that the hand is gripped between the support and the strap;

wherein the armband includes a main portion in cradle form, which, when the orthosis is worn by a user, covers the forearm, said main portion comprising a central portion placed against the rear face of the forearm and two lateral portions arranged on either side of the forearm, two distal lateral portions extending essentially longitudinally in the distal direction, each from a lateral portion of the main portion, on either side of the forearm, the pivot axis being situated essentially at the distal end portion of distal lateral pads.

* * * * *